US00PP21665P2

(12) United States Plant Patent
Geers

(10) Patent No.: US PP21,665 P2
(45) Date of Patent: Jan. 25, 2011

(54) ***EXOCHORDA* PLANT NAMED 'NIAGARA'**
(50) Latin Name: *Exochorda macranthaxExochorda racemosa*
Varietal Denomination: Niagara

(75) Inventor: Herman Geers, Boskoop (NL)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 12/653,194

(22) Filed: Dec. 9, 2009

(51) Int. Cl.
*A01H 5/00* (2006.01)

(52) U.S. Cl. ..... Plt./226
(58) Field of Classification Search ..... Plt./226

See application file for complete search history.

*Primary Examiner*—Annette H Para
(74) *Attorney, Agent, or Firm*—C. A. Whealy

(57) ABSTRACT

A new and distinct cultivar of *Exochorda* plant named 'Niagara', characterized by its compact, upright, outwardly spreading and mounding plant habit; easy to propagate; freely branching habit; freely flowering habit; large white-colored flowers; and good garden performance.

2 Drawing Sheets

Botanical designation: *Exochorda macranthaxExochorda racemosa.*

Cultivar denomination: 'NIAGARA'.

BACKGROUND OF THE INVENTION

The present invention relates to a new and distinct cultivar of *Exochorda* plant, botanically known as *Exochorda macranthaxExochorda racemosa* and hereinafter referred to by the name 'Niagara'.

The new *Exochorda* plant is a product of a planned breeding program conducted by the Inventor in Boskoop, The Netherlands. The objective of the breeding program is to develop new uniform *Exochorda* plants with fast rooting and good container performance.

The new *Exochorda* plant originated from a cross-pollination in 1994 *Exochorda macrantha* 'The Bride', not patented, as the female, or seed, parent with an unnamed selection of *Exochorda racemosa*, as the male, or pollen, parent. The new *Exochorda* plant was discovered and selected by the Inventor in 1997 as a single flowering plant within the progeny of the stated cross-pollination in a controlled environment in Boskoop, The Netherlands.

Asexual reproduction of the new *Exochorda* plant by softwood cuttings in a controlled greenhouse environment in Boskoop, The Netherlands since 1998 has shown that the unique features of this new *Exochorda* plant are stable and reproduced true to type in successive generations of asexual reproduction.

SUMMARY OF THE INVENTION

Plants of the new *Exochorda* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Niagara'. These characteristics in combination distinguish 'Niagara' as a new and distinct cultivar of *Exochorda:*

1. Compact, upright, outwardly spreading and mounding plant habit.
2. Easy to propagate.
3. Freely branching habit.
4. Freely flowering habit.
5. Large white-colored flowers.
6. Good garden performance.

Plants of the new *Exochorda* can be compared to plants of the female parent, 'The Bride'. Plants of the new *Exochorda* differ from plants of 'The Bride' in the following characteristics:

1. Plants of the new *Exochorda* are easier to propagate than plants of 'The Bride'.
2. Plants of the new *Exochorda* are more compact and mounding than plants of 'The Bride'.
3. Plants fo the new *Exochorda* have larger flowers than plants of 'The Bride'.

Plants of the new *Exochorda* can be compared to plants of the male parent selection. Plants of the new *Exochorda* differ from plants of the male parent selection in the following characteristics:

1. Plants of the new *Exochorda* are easier to propagate than plants of the male parent selection.
2. Plants of the new *Exochorda* are more compact than plants of the male parent selection.
3. Plants fo the new *Exochorda* are more freely flowering than plants of the male parent selection.

Plants of the new *Exochorda* can be compared to plants of *Exochorda serratifolia* 'Snow White', not patented. Plants of the new *Exochorda* differ primarily from plants of 'Snow White' in the following characteristics:

1. Plants of the new *Exochorda* are easier to propagate than plants of 'Snow White'.
2. Plants of the new *Exochorda* are more compact than plants of 'Snow White'.
3. Plants of the new *Exochorda* are not as vigorous as plants of 'Snow White'.

BRIEF DESCRIPTION OF THE PHOTOGRAPHS

The accompanying colored photographs illustrate the overall appearance of the new *Exochorda* plant, showing the colors as true as it is reasonably possible to obtain in colored reproductions of this type. Colors in the photographs may differ slightly from the color values cited in the detailed botanical description which accurately describe the colors of the new *Exochorda* plant.

The photograph on the first sheet is a side perspective view of a typical plant of 'Niagara' grown in an outdoor nursery.

The photograph on the second sheet is a close-up view of typical flowers and leaves of 'Niagara'.

DETAILED BOTANICAL DESCRIPTION

The aforementioned photographs and following observations, measurements and values describe plants of the new *Exochorda* grown in an outdoor nursery in Boskoop, The Netherlands during the spring under conditions which closely approximate commercial production. During the production of the plants, day temperatures ranged from 9° C. to 18° C. and night temperatures ranged from 1° C. to 12° C. Plants were four years old when the photographs and the description were taken. In the description, color references are made to The Royal Horticultural Society Colour Chart, 2007 Edition, except where general terms of ordinary dictionary significance are used.

Botanical classification: *Exochorda macrantha*×*Exochorda racemosa* 'Niagara'.

Parentage:

*Female, or seed, parent.*—*Exochorda macrantha* 'The Bride', not patented.

*Male, or pollen, parent.*—Unnamed selection of *Exochorda racemosa*, not patented.

Propagation:

*Type.*—By softwood cuttings.

*Time to initiate roots.*—Roots easily and quickly, about 25 days at 24° C.

*Time to produce a rooted young plant.*—About three months at 24° C.

*Root description.*—Fine to thick.

*Rooting habit.*—Freely branching; dense.

Plant description:

*Plant form and growth habit.*—Perennial shrub; compact, upright, outwardly spreading and mounding plant habit; moderately vigorous growth habit.

*Branching habit.*—Freely branching habit with about 35 primary lateral branches; pinching (removal of terminal apices) will enhance lateral branch development.

*Plant height.*—About 93.7 cm.

*Plant diameter* (*area of spread*).—About 92.6 cm.

Lateral branch description:

*Length.*—About 49.6 cm.

*Diameter.*—About 4 mm.

*Internode length.*—About 1.5 cm.

*Texture, developing.*—Smooth, glabrous.

*Texture, developed.*—Woody.

*Color, developing.*—Close to 144A to 144B.

*Color, developed.*—Close to N199B and 201A.

Foliage description:

*Arrangement.*—Alternate, simple.

*Length.*—About 7.4 cm.

*Width.*—About 3.8 cm.

*Shape.*—Elliptic to obovate.

*Apex.*—Retuse to obtuse.

*Base.*—Attenuate.

*Margin.*—Entire.

*Texture, upper and lower surfaces.*—Smooth, glabrous.

*Venation pattern.*—Pinnate.

*Color.*—Developing leaves, upper surface: Close to 144A. Developing leaves, lower surface: Close to 144A to 144B. Fully expanded leaves, upper surface: Between 137A and 139A; venation, close to 145A to 145B. Fully expanded leaves, lower surface: Between 137C and 138A; venation, close to 145B.

*Petiole.*—Length: About 1.9 cm. Diameter: About 1 mm. Texture, upper and lower surfaces: Smooth, glabrous. Color, upper and lower surfaces: Close to 145B.

Flower description:

*Flower appearance/arrangement.*—Single rotate flowers arranged in terminal and axillary racemes; freely flowering habit with usually about nine flowers per inflorescence and about 198 flowers and flower buds per lateral branch; flowers face upright to outwardly.

*Natural flowering season.*—Plants of the new *Exochorda* flower during April in The Netherlands.

*Flower longevity.*—Flowers last about twelve days on the plant; flowers not persistent.

*Fragrance.*—None detected.

*Inflorescence height.*—About 5.2 cm.

*Inflorescence diameter.*—About 3.3 cm.

*Flower diameter.*—About 3.3 cm.

*Flower length* (*height*).—About 1.2 cm.

*Flower bud.*—Length: About 6 mm. Diameter: About 6 mm. Shape: Rhomboidal. Color: Between 145D and 150D; calyx, close to 145A to 145B.

*Petals.*—Quantity per flower: Single whorl of five. Length: About 1.5 cm. Width: About 1.5 cm. Shape: Broadly obovate to spatulate. Apex: Obtuse to broadly retuse. Margin: Entire. Texture, upper and lower surfaces: Smooth, glabrous; slightly rugose. Color: When opening, upper and lower surfaces: Close to 155A to 155C. Fully opened, upper and lower surfaces: Close to NN155D.

*Sepals.*—Quantity per flower: Single whorl of five, fused towards the base. Length: About 4 mm. Width: About 3 mm. Shape: Broadly elliptic to orbicular. Apex: Rounded. Margin: Finely denticulate. Texture, upper and lower surfaces: Smooth, glabrous. Color: When opening, upper and lower surfaces: Close to 145A to 145B. Fully opened, upper surface: Close to 157B. Fully opened, lower surface: Close to 150D.

*Peduncles.*—Length: About 4 cm. Diameter: About 1 mm. Strength: Moderately strong. Aspect: Erect to about 45° from the lateral branch axis. Texture: Smooth, glabrous. Color: Close to 145A.

*Pedicels.*—Length: About 2 mm. Diameter: About 0.75 mm. Strength: Moderately strong. Aspect: About 45° from the peduncle axis. Texture: Smooth, glabrous. Color: Close to 145A.

*Reproductive organs.*—Androecium: Quantity per flower: About 25. Filament length: About 2 mm. Anther shape: Reniform. Anther length: About 0.75 mm. Anther color: Close to 161B. Amount of pollen: Scarce. Pollen color: Close to 161C to 161D. Gynoecium: Quantity per flower: Five. Pistil length: About 1.5 mm. Style length: About 1.2 mm. Style color: Close to 143A to 143B. Stigma appearance: Flattened globose. Stigma color: Close to 144A. Ovary color: Close to 137A.

*Seeds.*—Length: About 6.5 mm. Diameter: About 2 mm to 5 mm. Color: Close to 200D.

Garden performance: Plants of the new *Exochorda* have been observed to have good garden performance and to tolerate rain, wind and temperatures ranging from about −29 C. to about 38° C.

Pathogen/pest resistance: Plants of the new *Exochorda* have not been observed to be resistant to pathogens and pests common to *Exochorda.*

It is claimed:

1. A new and distinct *Exochorda* plant named 'Niagara' as illustrated and described.

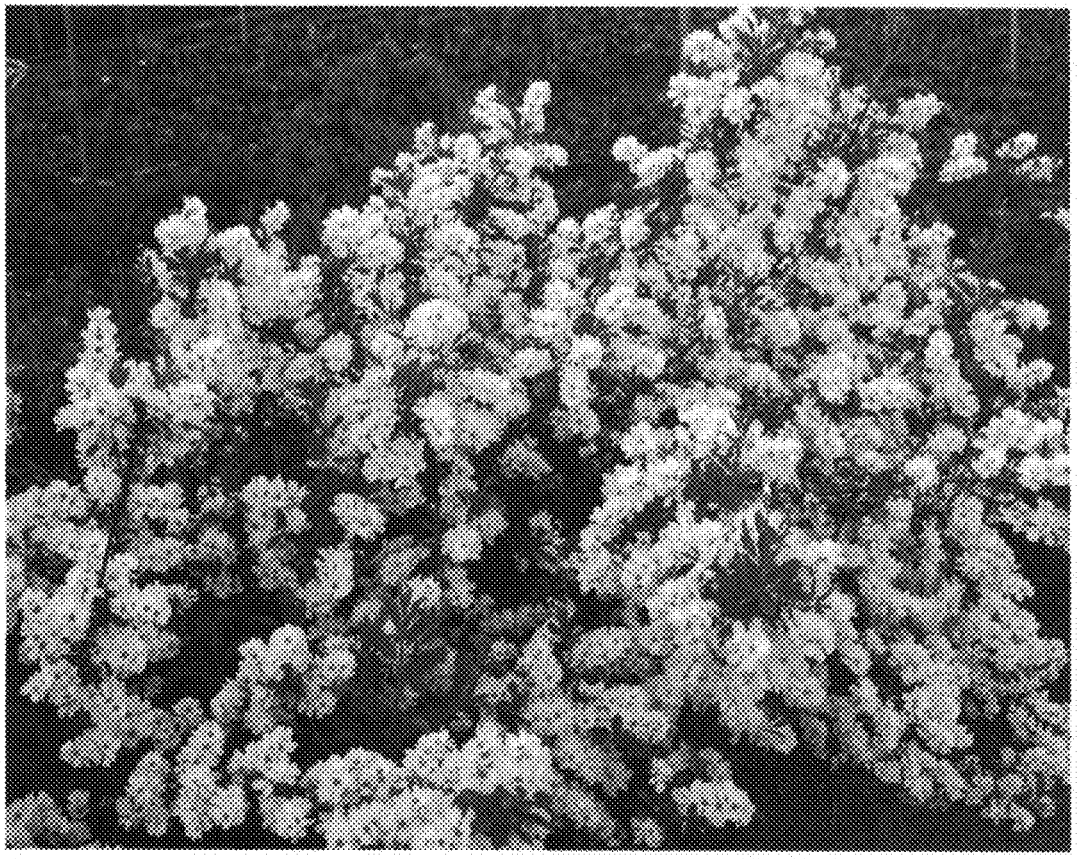

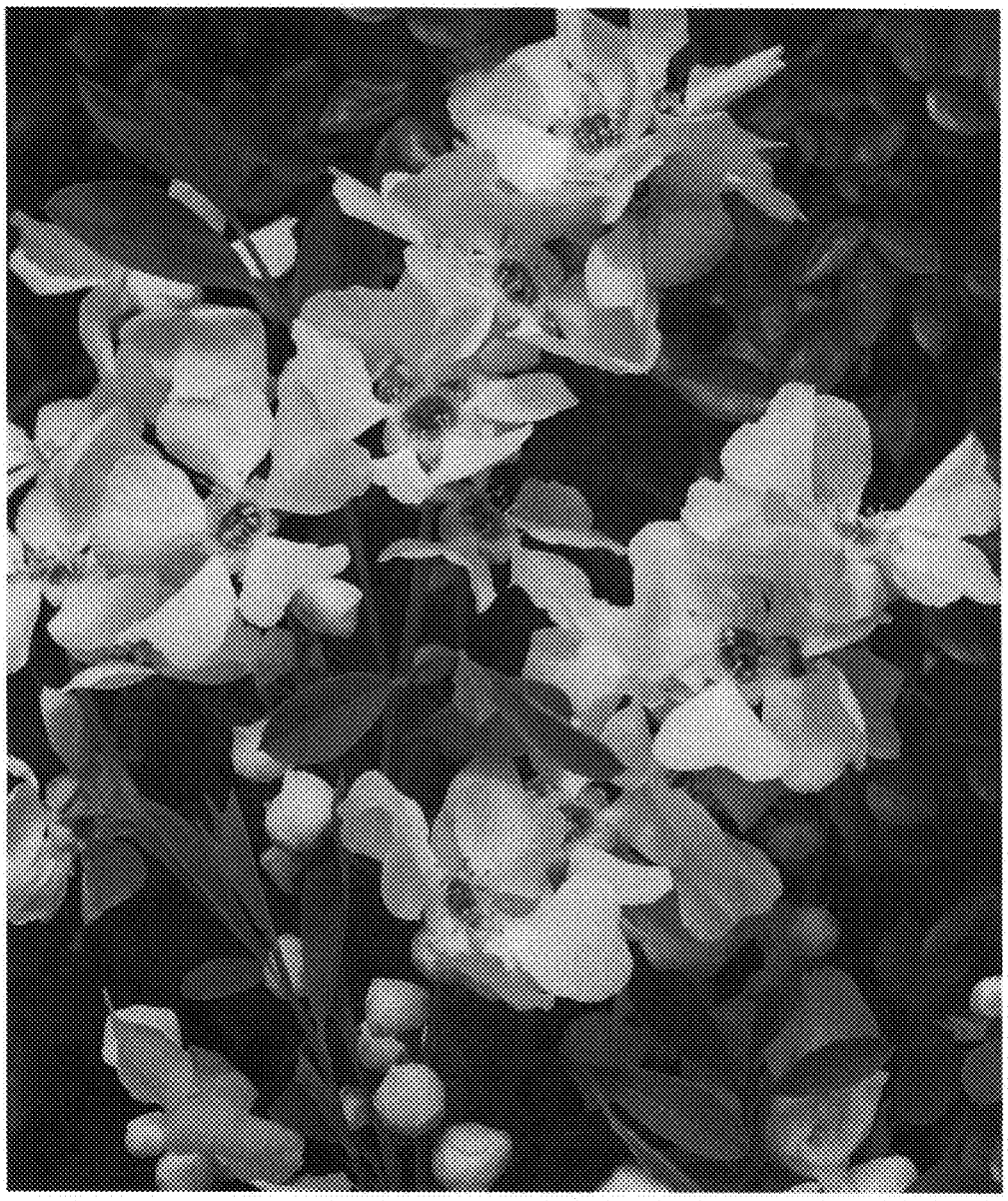

* * * * *